United States Patent [19]

Mahoney

[11] 4,222,378
[45] Sep. 16, 1980

[54] MOUTHPIECE ACCESSORY AND SEAL

[76] Inventor: Dennis C. Mahoney, 139 Salem St., Apt. 5, Boston, Mass. 02113

[21] Appl. No.: 954,238

[22] Filed: Oct. 24, 1978

[51] Int. Cl.³ .............................................. A61M 16/00
[52] U.S. Cl. ............................ 128/206.24; 128/207.14
[58] Field of Search .................... 128/147, 208, 145 A, 128/351, 201, 136, 206.24, 207.14

[56] References Cited

U.S. PATENT DOCUMENTS

| 3,013,554 | 12/1961 | Safar et al. ........................ 128/351 X |
| 3,303,845 | 2/1967 | Detmer ............................ 128/147 X |
| 3,692,025 | 9/1972 | Greenberg ............................ 128/136 |
| 4,030,493 | 6/1977 | Walters et al. ........................ 128/147 |
| 4,090,518 | 5/1978 | Elam ................................ 128/351 X |

Primary Examiner—Henry J. Recla
Attorney, Agent, or Firm—Herbert L. Gatewood

[57] ABSTRACT

An ovate convex-concave shaped flexible mouthpiece accessory and seal for a positive pressure breathing apparatus mouthpiece having a continuous raised edge of uniform shape and dimension along the edge of the concave side of the faceplate and a rectangular shaped, shape-retaining tube extending perpendicularly outwardly from the concave side at the center of the faceplate and integral with an oval shaped opening in the faceplate.

1 Claim, 4 Drawing Figures

MOUTHPIECE ACCESSORY AND SEAL

BACKGROUND OF THE INVENTION (1) Field Of The Invention

This invention relates to an intermittent positive pressure breathing apparatus and, in particular, to an improved mouthpiece accessory for that apparatus.

(2) Description Of The Prior Art

While an intermittent positive pressure breathing (IPPB) apparatus is commonly used whenever a patient needs ventilation, such an apparatus also is used in respiratory therapy, to supply liquid medication in aersol form to, e.g., the lungs and bronchi. Such an apparatus, in general, functions to provide gaseous pressure for inhalation by a patient, until the patient's lungs expand and sufficient back pressure is built up to cause the inward pressure to automatically terminate, and allow the patient to exhale, before pressure is again applied by the breathing apparatus.

The positive pressure breathing apparatus comprises an elongated flexible tube which is connected at one end with a gas delivery apparatus. The other end of the tube, i.e., the free end, is provided with a mouthpiece for introduction into a patient's mouth, between his teeth. Where the patient is conscious and cooperative, and is able to, the patient grips the mouthpiece between his teeth and, in this way, the mouthpiece is retained within his mouth. Thus, a seal is maintained to prevent loss of gaseous pressure. Where gaseous pressure is lost, as by the escape of gas from the patient's mouth, sufficient back pressure is often not built up to shut off the incoming gas, to terminate the inhalation cycle. Accordingly, the patient is prevented from exhaling, as desired.

In many cases, however, the patient may be under an anesthetic or infirm, or otherwise unable on his own, to retain the mouthpiece within his mouth. Thus, it becomes necessary, not only to place the mouthpiece within the patient's mouth, but also provide that it is retained within the patient's mouth, as desired, and that a proper seal is provided against escape of gas. One means of accomplishing this is shown in U.S. Pat. No. 2,857,911. Another more recent mouthpiece accessory and seal is disclosed in U.S. Pat. No. 4,030,493.

As disclosed in U.S. Pat. No. 4,030,493 the mouthpiece of the positive pressure breathing apparatus can be provided with a disposable flexible ovate convex, concave shaped faceplate which can be pressed against the areas above and below a patient's mouth and the areas adjacent the mouth extremities. That disposable faceplate is characterized by a ridge on the periphery of the concave side that tapers toward the faceplate in both directions from the center of the faceplate. Thus, a ridge is provided which is of the greatest height at the center, and of lesser height at the extremities of the ovate shape. Moreover, the width of the ridge at the extremities, as disclosed in the patent, is considerably less than in the center sections.

While either of these mouthpieces now commercially used has been satisfactory to a degree, neither has provided entirely satisfactory performance. The mouthpiece disclosed in U.S. Pat. No. 2,857,911 is not only generally not disposable because of its cost, its construction does not lend itself to ease in cleaning, for re-use. Even though the mouthpiece accessory disclosed in U.S. Pat. No. 4,030,493 is of quite simple construction, and its manufacture economical so that its cost permits it to be disposable, the structural features of that mouthpiece does not always provide an adequate seal against escaping gas.

SUMMARY OF THE INVENTION

In accordance with the major objects of the invention there is provided an economically manufactured, disposable mouthpiece accessory for an intermittent positive pressure breathing apparatus mouthpiece, not attendant with the problems of those heretofore used.

Quite advantageously, the mouthpiece accessory according to the invention provides a positive seal against escape of gas and does so without regard to the various and different conformities of the area above and below a patient's mouth and the areas adjacent the mouth extremities, found with different patients. Thus, a mouthpiece is provided that provides a more positive seal with more universal application.

The mouthpiece accessory of the invention comprises, in its basic aspects, an ovate, flexible, convex-concave shaped faceplate having on its concave side a raised edge of arcuate cross section and uniform height and width extending outwardly from the concave surface of the faceplate along the entire upper and lower perimeters of the ovate shape and an inwardly directed elongated oval shaped opening centrally located in the faceplate, and a rectangular shaped, shape-retaining tube extending perpendicularly outwardly from the concave surface of the faceplate integral with the elongated oval shaped opening.

BRIEF DESCRIPTION OF THE DRAWING

The features of the invention will be better understood by reference to the accompanying drawing in connection with reading the specification in which.

DETAILED DESCRIPTION OF THE INVENTION AND THE PREFERRED EMBODIMENTS

Figure 1:
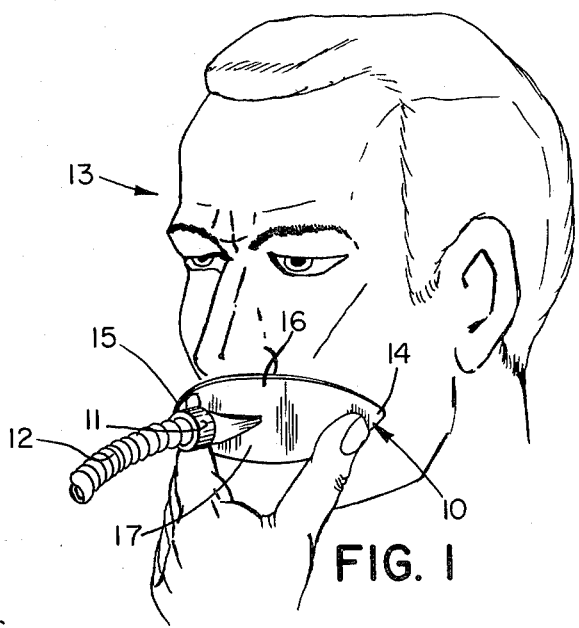
FIG. 1 is a perspective view showing the use of the mouthpiece accessory of my invention on the mouthpiece end of an intermittent positive pressure breathing apparatus.

Turning now to the drawing, there is shown in FIG. 1 thereof, a flexible, ovate, convex-concave shaped mouthpiece accessory 10 according to the invention in association with a conventional mouthpiece 11 attached to the free end of a flexible tube 12, the other end of which is connected to the gas delivery apparatus, e.g., an intermittent positive pressure breathing apparatus (IPPB), not shown.

As shown in the drawing, the mouthpiece extends into the mouth of the patient 13, according to usual fashion, and between his teeth or gums, if the patient has no teeth. The ends 14, 15 of the mouthpiece accessory 10 are pressed, as shown, by an attendant's thumb and fingers against the patient's cheeks of areas adjacent the extremities of the mouth. Thus, the upper and lower edges 16, 17 of the mouthpiece accessory 10 are pressed inwardly against the areas above and below the patient's mouth, and a positive seal against the escape of gas is provided.

Mouthpiece accessory 10 comprises a flexible faceplate characterized by an ovate convex-concave shape defined by relatively pointed ends or extremities 14, 15, symmetrical with respect to one another. The convex front surface 18 and concave back surface 19 of the mouthpiece accessory 10 are smooth. The concavity of the mouthpiece accessory 10 is such as to generally conform to a patient's mouth area. However, its flexibility provides that the mouthpiece can be made with light pressure to conform more as desired, to provide a proper seal.

Figure 2:
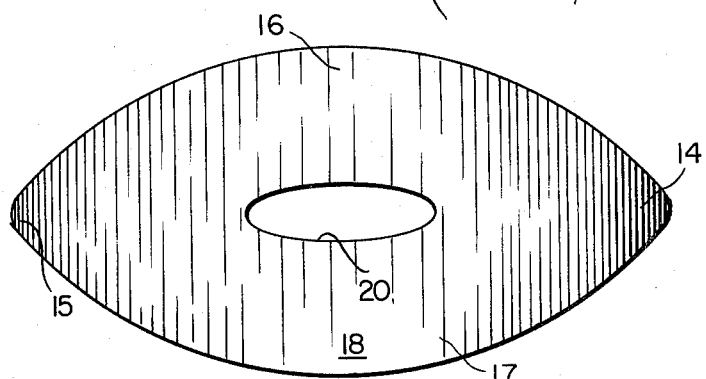
FIG. 2 is a plan view of the front of the mouthpiece accessory shown in FIG. 1 detached from the mouthpiece.

An elongated oval shaped opening 20 is provided in mouthpiece accessory 10, as shown in FIG. 2 of the drawing. Opening 20 is located centrally of the mouthpiece accessory and its long direction extends in the long direction of the ovate shaped faceplate. The oval shaped opening 20 extends inwardly from convex surface 18 to concave surface 19. This opening is of a sufficient size and dimension to snugly fit with the conventional mouthpiece 11 on the end of flexible tube 12, so that a good seal is provided against the escape of gas.

Figure 3:
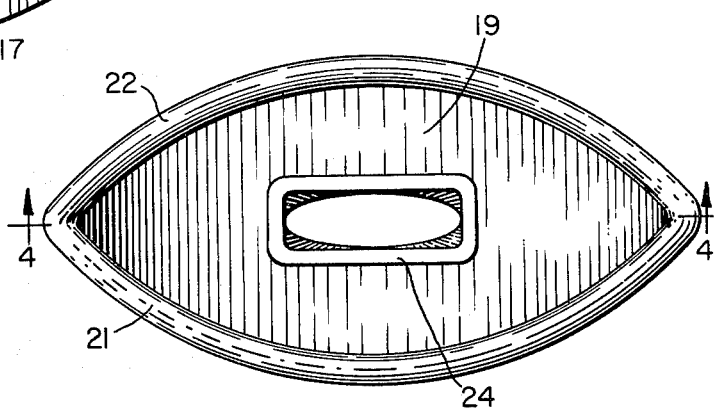
FIG. 3 is a plan view of the back side of the mouthpiece accessory shown in FIG. 2.
Figure 4:
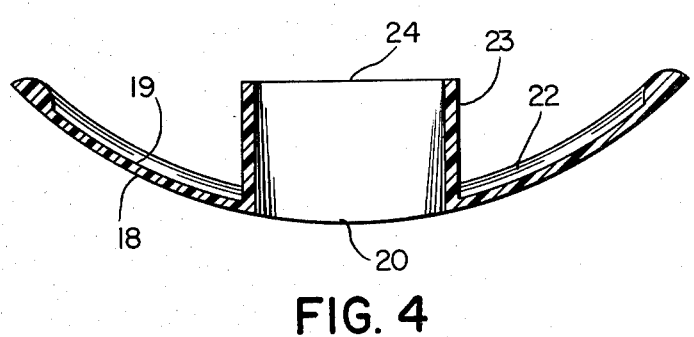
FIG. 4 is a view in section of the mouthpiece according to the invention, taken at secant lines 4—4.

As shown more clearly in FIG. 3 of the drawing, a raised edge 21, 22 is provided along the entire periphery of the upper and lower edges 16, 17, of the mouthpiece accessory 10. These edges are integral with and extend outwardly from the concave surface 19 of the mouthpiece accessory. Critically, raised edges 21, 22 are of uniform arcuate shape and dimension along the upper and lower edges of the faceplate. The arcuate shape provides not only ease of comfort to a patient, but provides a shape having good sealing characteristics. The ends of raised edges 21, 22 meet with one another at the extremities 14, 15 of the ovate shaped mouthpiece accessory 10, and are integrally joined together as a unit.

On the concave side of the mouthpiece accessory 10, there is provided a somewhat elongated rectangular shaped tube 23 which extends perpendicularly outwardly from concave surface 19. Rectangular shaped tube 23 is integral with concave surface 19 and, as shown in FIG. 3, is in coaxial relationship with oval shaped opening 20 and provides a smooth surfaced continuous elongated opening extending inwardly from the convex side of the mouthpiece accessory 10 and from the concave side thereof. Thus, there is provided an opening 20 at the outer end of which is of an oval shape and the inner end 24 of which is of a rectangular shape. This particular configuration has been found to not only conform well with mouthpiece 11 but to provide a more positive seal against escape of gas through extended usage of the disposable mouthpiece accessory.

Rectangular shaped tube 23 should be of sufficient thickness, depending somewhat on the particular materials used in the manufacture of the mouthpiece accessory 10, to retain its rectangular shape. The tube should also be sufficiently flexible to provide a comfortable feel to a patient's mouth. The optimum feel will, of course, differ with the patient. However, in general the tube should not be so stiff as to be rigid, and not be compressible with finger pressure. The more flexible, yet shape retaining the tube is, the more comfortable it will feel to a patient.

The mouthpiece accessory of the invention can be manufactured by conventional molding techniques e.g., injection molding and the like, and can be manufactured from various elastomeric and plastic materials, preferably an elastomeric material, as these will provide a somewhat better seal. Elastomeric materials have better elasticity or give which allows the mouthpiece accessory opening to be somewhat stretched for insertion of the mouthpiece through the opening, yet a memory or shape retention characteristic that retains the original dimensions of the opening, to provide a tight seal around the mouthpiece. Various materials commercially available will be found satisfactory for the intended use and desired characteristics, such as the Kraton thermoplastic rubbers, available commercially from Shell Chemical Company. Kraton 2104, a block copolymer of butadiene-styrene, will be found particularly suitable as it results in a product having a Shore hardness of about 43. While elastomeric materials resulting in a mouthpiece accessory having a less hard or more hard characteristic can be used, the resulting product should be sufficiently shape retaining that a proper seal can be formed, yet not too inflexible as to be uncomfortable to a patient on pressing against the mouth area or in the mouth cavity. The faceplate should feel soft to one's mouth.

Other materials that might be used in the practice of the invention, but are of somewhat less desirable characteristics, include natural rubber and various other synthetic rubbery materials such as other butadiene copolymers and various plastic materials such as the vinyl chloride polymers and copolymers, nylon, polyethylene, and the like. These materials can be compounded with various fillers, according to usual techniques, to provide a product of desired characteristics.

While the particular dimensions of the ovate faceplate will depend somewhat upon the individual receiving respiratory therapy, particularly whether an adult or child is involved, a somewhat universal size will be found in a faceplate curved essentially cylindrically, preferably with a radius of curvature of approximately 1¾ inches. The faceplate will desirably be also slightly concave in a direction from the top edge to the bottom edge, making the faceplate concave in both its long and short directions. The thickness will depend somewhat on the particular material of construction, keeping in mind the desired combination of stiffness and flexibility. However, in general a thickness of about 7/64 inches will be found satisfactory.

As to raised edges 21, 22 the main consideration is that they be arcuate and of uniform size and dimension along their entire length. The height of the raised edges above the concave surface should preferably be about equal to the thickness of the accompanying faceplate. The arcuate shaped edge should be about ¼ inch at its base.

The dimensions of the openings depend somewhat, of course, upon the particular mouthpiece dimensions. However, for most applications, an oval shaped inlet measuring 1 6/32" × 13/32" (length × width) will be found satisfactory. The rectangular shaped opening in this case will measure internally the same, and have a thickness about 5/64 inches.

A particularly suitable faceplate according to this invention can be manufactured from Kraton 2104-1002-3 (Natural 08ZDD-2001, a butadiene-styrene copolymeric material available from Shell Chemical Company. This material can be injection molded under high pressure, e.g., about 3000 pounds per square inch, at 400° F.

As many different embodiments of this invention will occur to those skilled in the art, it is to be understood that the specific embodiments of the invention as presented herein are intended by way of illustration only and are not limiting on the invention, but that the limitations thereon are to be determined only from the appended claims.

What I claim is:

1. Mouthpiece accessory for use with the mouthpiece for an intermittent positive pressure breathing apparatus to provide a seal against the escape of gas and permit the incoming gases to be inhaled comprising a flexible faceplate characterized by an ovate convex-concave shape conforming to a patient's mouth area, the extremities of which ovate shape are symmetrical with respect to one another and are characterized by being relatively pointed, an oval shaped opening in the center of said faceplate extending inwardly from the convex side thereof to the concave side, and a rectangular shaped flexible, shape-retaining tube extending perpendicularly outwardly from the concave side of the mouthpiece integral with said concave side and in coaxial relationship with said oval shaped opening in the faceplate, and a raised, arcuate-shaped, edge of uniform height and width extending outwardly on the concave side of the faceplate and extending along the entire upper and lower perimeters of the ovate shape, said upper and lower raised edges joining with one another at the ovate extremities whereby a continuous raised edge is provided along the entire inner periphery of the faceplate.

* * * * *